United States Patent
Talton

(10) Patent No.: US 9,554,996 B2
(45) Date of Patent: *Jan. 31, 2017

(54) COMPOSITIONS AND METHODS FOR DELIVERY OF POORLY SOLUBLE DRUGS

(71) Applicant: Nanotherapeutics, Inc., Alachua, FL (US)

(72) Inventor: James David Talton, Alachua, FL (US)

(73) Assignee: NANOTHERAPEUTICS, INC., Alachua, FL (US)

(*) Notice: Subject to any disclaimer, the term of this patent is extended or adjusted under 35 U.S.C. 154(b) by 654 days.

This patent is subject to a terminal disclaimer.

(21) Appl. No.: 13/741,915

(22) Filed: Jan. 15, 2013

(65) Prior Publication Data

US 2013/0129828 A1  May 23, 2013

Related U.S. Application Data

(63) Continuation of application No. 12/202,881, filed on Sep. 2, 2008, now Pat. No. 8,377,479.

(60) Provisional application No. 60/969,672, filed on Sep. 3, 2007.

(51) Int. Cl.

| | |
|---|---|
| *A61K 9/14* | (2006.01) |
| *A61K 9/50* | (2006.01) |
| *A61P 25/30* | (2006.01) |
| *A61P 25/36* | (2006.01) |
| *A61K 31/485* | (2006.01) |
| *A61K 9/48* | (2006.01) |

(52) U.S. Cl.
CPC ............. *A61K 9/146* (2013.01); *A61K 9/5021* (2013.01); *A61K 9/5026* (2013.01); *A61K 9/5031* (2013.01); *A61K 31/485* (2013.01); *A61K 9/4866* (2013.01)

(58) Field of Classification Search
None
See application file for complete search history.

(56) References Cited

U.S. PATENT DOCUMENTS

| | | |
|---|---|---|
| 4,525,339 A | 6/1985 | Behl et al. |
| 4,722,941 A | 2/1988 | Eckert et al. |
| 5,145,684 A | 9/1992 | Liversidge et al. |
| 5,190,748 A | 3/1993 | Bachynsky et al. |
| 5,318,781 A | 6/1994 | Shah et al. |
| 5,858,531 A | 1/1999 | Chenite et al. |
| 5,866,164 A | 2/1999 | Kuczynski et al. |
| 5,908,697 A * | 6/1999 | Roux et al. ............. 428/402.2 |
| 5,958,452 A | 9/1999 | Oshlack et al. |
| 5,981,719 A | 11/1999 | Woiszwillo et al. |
| 6,190,699 B1 | 2/2001 | Luzzi et al. |
| 6,235,313 B1 | 5/2001 | Mathiowitz et al. |
| 6,248,360 B1 | 6/2001 | Choi et al. |
| 6,261,599 B1 | 7/2001 | Oshlack et al. |
| 6,270,806 B1 | 8/2001 | Liversidge et al. |
| 6,368,586 B1 | 4/2002 | Jacob et al. |
| 6,406,745 B1 | 6/2002 | Talton |
| 6,733,789 B1 * | 5/2004 | Stark ................. A61K 9/5078 424/451 |
| 6,743,442 B2 | 6/2004 | Oshlack et al. |
| 7,157,102 B1 | 1/2007 | Nuwayser |
| 7,316,821 B2 | 1/2008 | Oshlack et al. |
| 7,384,653 B2 | 6/2008 | Wright, IV et al. |
| 8,377,479 B2 * | 2/2013 | Talton ...................... 424/490 |
| 2001/0027614 A1 | 10/2001 | Chickering, III et al. |
| 2002/0012675 A1 | 1/2002 | Jain et al. |
| 2002/0012700 A1 * | 1/2002 | Johnson et al. ............ 424/464 |
| 2002/0106461 A1 * | 8/2002 | Talton ...................... 427/596 |
| 2003/0004178 A1 | 1/2003 | Chapleo et al. |
| 2003/0162835 A1 * | 8/2003 | Staniforth et al. .......... 514/561 |
| 2004/0110781 A1 | 6/2004 | Harmon et al. |
| 2004/0191301 A1 * | 9/2004 | Van Duren .................. 424/449 |
| 2005/0048115 A1 | 3/2005 | Mangena et al. |
| 2005/0079138 A1 | 4/2005 | Chickering, III et al. |
| 2005/0175707 A1 | 8/2005 | Talton et al. |
| 2005/0181046 A1 * | 8/2005 | Oshlack ............... A61K 9/0043 424/468 |
| 2007/0020339 A1 | 1/2007 | Bear |
| 2008/0260844 A1 | 10/2008 | Soula et al. |

FOREIGN PATENT DOCUMENTS

| | | |
|---|---|---|
| EP | 0 012 523 | 6/1980 |
| EP | 0 605 024 | 7/1994 |

(Continued)

OTHER PUBLICATIONS

SM Berge, LD Bighley, DC Monkhouse. "Pharmaceutical Salts." Journal of Pharmaceutical Sciences, vol. 66 No. 1, Jan. 1977, pp. 1-19.*

(Continued)

*Primary Examiner* — Isaac Shomer
(74) *Attorney, Agent, or Firm* — Finnegan, Henderson, Farabow Garrett & Dunner LLP

(57) ABSTRACT

Described herein are compositions comprising particles of poorly soluble drugs encapsulated by stabilizers. Further described are pharmaceutical compositions comprising such encapsulated compositions. Also described are methods of making such encapsulated particle compositions, and methods of making the corresponding pharmaceutical compositions. The encapsulated particle compositions described herein allow poorly soluble drugs to be administered with good bioavailability by routes that are non-invasive to patients, such as by oral administration.

11 Claims, No Drawings

(56) References Cited

FOREIGN PATENT DOCUMENTS

| | | | |
|---|---|---|---|
| EP | 0 631 781 | 1/1995 | |
| EP | 1 752 142 | 2/2007 | |
| GB | 1 456 618 | 11/1976 | |
| LU | EP 0631781 A1 * | 1/1995 | ........... A61K 9/1617 |
| RU | 2228180 C2 | 5/2004 | |
| RU | 2241458 C2 | 12/2004 | |
| RU | 2253452 C2 | 6/2005 | |
| WO | WO 91/14423 | 10/1991 | |
| WO | WO 95/27482 | 10/1995 | |
| WO | WO 01/15699 | 3/2001 | |
| WO | WO 2004/087097 | 10/2004 | |
| WO | WO 2006/056713 | 6/2006 | |
| WO | WO 2007/008480 | 1/2007 | |

OTHER PUBLICATIONS

Avanti No. 880430, "Long Circulating Liposomes and Membrane Tagging," Poly(Ethylene Glycol)-Lipid Conjugates, 18:1 PEG350 PE (2001), www.avantilipids.com.

Awasthi, V.D. et al. "Neutral and Anionic Liposome-Encapsulated Hemoglobin: Effect of Postinserted Poly(ethylene glycol)-distearoylphosphatidylethanolamine on Distribution and Circulation Kinetics," The Journal of Pharmacology and Experimental Therapeutics. vol. 309, 2004, pp. 241-248.

Berge, S.M., et al., DC Monkhouse, "Pharmaceutical Salts," Journal of Pharmaceutical Sciences, vol. 66 No. 1, Jan. 1977, pp. 1-19.

Clark, H.W., Department of Health and Human Services, Substance Abuse and Mental Health Services Administration, Apr. 3, 2006, 2 pages.

Couvreur, P., "Aspects Pharmaco-Toxicologiques et Biopharmaceutiques," Nanotechnologies et Interaction Avec Les Tissus, 2009-2010.

Crowe, J.H. et al., "Preservation of Dry Liposomes does not require Retention of Residual Water", Proc. Natl. Acad. Sci., Biophysics, vol. 84, Mar. 1987, pp. 1537-1540.

De Jaeghere et al., AAPS Pharmsci, 3(1):1-8, Article 8 (2001).

De Jaeghere et al., J. Controlled Release, 68:291-298 (2000).

Derwent Abstract of WO 9114423 A (1991).

Hede, P.D., Fluid Bed Particle Processing, www.ventus.dk, pp. 3-80, downloaded from Download free books at BookBoon.com, Jan. 2009.

International Search Report for PCT Application No. PCT/US2008/010318 dated Mar. 16, 2009.

Kabanov et al., "A New Class o f Drug Carriers: Micelles o f Poly(Oxyethylene)-Poly(Oxyp Propylene) Block Copolymers as Microcontainers for Drug Targeting from Blood in Brain 1," Journal of Controlled Release vol. 22, No. 2, Oct. 1992, pp. 141-157.

Kayumba, P.C. et al., "Quinine Sulphate Pellets for Flexible Pediatric Drug Dosing: Formulation Development and Evaluation of Taste-Masking Efficiency using the Electronic Tongue " European Journal of Pharmaceutics and Biopharmaceutics, Dec. 19, 2006, available online at www.sciencedirect.com.

Lu, D. et al., "Liposomal Dry Powders as Aerosols for Pulmonary Delivery of Proteins," AAPS PharmSciTech, 6(4) 2005, Article 80 (http://www.aaospharmscitech.org), pp. E641-E-648.

Machine Translation of Ishikawa et al. (WO 91/14423 A, published in Japanese in Oct. 1991). The machine translation is 15 printed pages.

Sheen, P.C. et al., "Formulation Studies of a Poorly Water-Soluble Drug in Solid Dispersions to Improve Bioavailability," International Journal of Pharmaceutics, vol. 118, No. 2, 1995, pp. 221-227.

Sun, W.Q. et al., "Stability of Dry Liposomes in Sugar Glasses," Biophysical Journal, vol. 70, Apr. 1996, pp. 1769-1776.

Tirosh, O. et al., "Hydration of Polyethylene Glycol-Grafted Liposomes," Biophysical Journal, vol. 74, Mar. 1998, pp. 1371-1379.

Supplementary International Search Report for PCT Application No. PCT/US2008/010318 dated Feb. 25, 2010.

* cited by examiner

COMPOSITIONS AND METHODS FOR DELIVERY OF POORLY SOLUBLE DRUGS

This is a continuation of U.S. patent application Ser. No. 12/202,881, filed Sep. 2, 2008, and claims the benefit of U.S. Provisional Application No. 60/969,672, filed Sep. 3, 2007, all of which are incorporated herein by reference.

The U.S. Government has a paid-up license in this invention and the right in limited circumstances to require the patent owner to license others on reasonable terms as provided for by the terms of Contract No. HHSN271200577414C awarded by the National Institute on Drug Abuse.

FIELD OF THE INVENTION

The present invention relates generally to compositions comprising particles of poorly soluble drugs encapsulated by stabilizers, and to pharmaceutical compositions comprising such encapsulated compositions. It further relates to methods of making such encapsulated particle compositions, and to methods of making the corresponding pharmaceutical compositions. The encapsulated particle compositions described herein allow poorly soluble drugs to be administered with good bioavailability by routes that are non-invasive to patients, such as by oral administration.

BACKGROUND

Oral administration of drugs is generally preferred for reasons of patient comfort and compliance. However, many drugs, including many opioids, are poorly soluble at neutral pH, and are thus are poorly or variably absorbed when delivered orally. Consequently, many such drugs are administered through more invasive routes, such as by sublingual, buccal, subcutaneous, or intravenous routes.

Several approaches for improving the oral delivery of poorly soluble drugs have demonstrated some promise. For example, poorly soluble drugs have been administered as dispersions in large amounts of fatty acids, and have been wet-milled to yield nanoparticles. However, each of those approaches suffers from certain drawbacks, such as, e.g., inadequate stability, difficulty of manufacture, adverse interactions with the drug to be delivered, or the use of toxic amounts of adjuvants or inhibitors. Thus, there remains a need for compositions and methods for the non-invasive delivery of poorly soluble drugs.

SUMMARY

In some embodiments, the invention provides a composition comprising particles of a poorly soluble drug (such as, e.g., an opioid) encapsulated by a stabilizer. The stabilizer may be, e.g., a polymer, including, e.g., a water-soluble polymer of neutral charge. For example, in some embodiments, the invention provides a composition comprising particles of buprenorphine encapsulated by PEG, wherein the buprenorphine content ranges from about 0.2% to about 4%. In other embodiments, the composition further comprises a surfactant, such as, e.g., a polysorbate surfactant.

In other embodiments, the invention provides pharmaceutical compositions comprising such encapsulated compositions. Such pharmaceutical compositions may, in some embodiments, further comprise at least one excipient. In other embodiments, such pharmaceutical compositions may further comprise a second compound such as, e.g., a second drug, including, e.g., an opioid receptor antagonist, an anti-inflammatory drug, or an analgesic. For example, in some embodiments, the invention provides a pharmaceutical composition comprising a composition comprising the PEG-encapsulated buprenorphine composition described above. In certain embodiments, the pharmaceutical composition further comprises naloxone.

In some embodiments, the invention provides a first method of making a composition comprising particles of a poorly soluble drug encapsulated by a stabilizer, the method comprising:
　blending a poorly soluble drug together with a stabilizer to form a mixture;
　processing said mixture to form coarse particles having an average diameter ranging from about 0.1 mm to about 5 mm; and
　processing said coarse particles to form fine particles having an average diameter ranging from about 0.1 mm to about 3 mm.

In some embodiments, the invention provides a second method of making a composition comprising particles of a poorly soluble drug encapsulated by a stabilizer, the method comprising:
　blending a poorly soluble drug together with a stabilizer to form a mixture;
　heating said mixture to a temperature sufficient for extrusion of the mixture;
　extruding said mixture to form coarse particles having an average diameter ranging from about 0.1 mm to about 5 mm;
　cooling said coarse particles; and
　processing said coarse particles to form fine particles having an average diameter ranging from about 0.1 mm to about 3 mm.

In further embodiments, the invention provides a method of making a pharmaceutical composition, comprising the first or second method described above, and further comprising:
　formulating the fine particles.

In further embodiments, the invention provides a method of making a pharmaceutical composition, comprising the first or second method described above, and further comprising:
　mixing the fine particles with at least one excipient to form a second mixture; and
　formulating the second mixture.

In yet other embodiments, the invention provides a method of treating pain, comprising administering the pharmaceutical composition described above to a patient in need thereof. In other embodiments, the invention provides a method of treating opiate addiction, comprising administering the pharmaceutical composition described above to a patient in need thereof.

DETAILED DESCRIPTION

I. Particulate Delivery Systems

In some embodiments, the invention provides a composition (also referred to as a particulate delivery system or PDS) comprising particles of a poorly soluble drug encapsulated by a stabilizer. In some embodiments, those particles are fine particles, and have a diameter of less than 3 mm, less than 2 mm, less than 600 μm, less than 500 μmm, or less than 300 μm. In some embodiments, the fine particles have an average diameter ranging from about 0.1 mm (100 μm) to about 3 mm. For example, the particles may have a diameter of less than 2.06 mm (corresponding to a 10 mesh sieve), less than 1.68 mm (corresponding to a 12 mesh sieve), less than 1.40 mm (corresponding to a 14 mesh sieve), less than 1.20 mm (corresponding to a 16 mesh sieve), less than 1.00 mm (corresponding to an 18 mesh sieve), less than 0.853 mm (corresponding to a 20 mesh sieve), less than 0.710 mm (corresponding to a 25 mesh sieve), less than 0.599 mm (corresponding to a 30 mesh sieve), or less than 0.500 mm (corresponding to a 35 mesh sieve). In other embodiments, the particles may have a diameter of less than 300 µm, and may be able to pass through a 50 mesh sieve.

As used herein, the term drug encompasses the corresponding salts, hydrates, solvates, prodrugs, and complexes of the drug. Thus, the drug may be present as, e.g., a free base, a salt, a hydrate, a prodrug, a solvate (including a mixed solvate), or a complex (such as a pharmaceutically acceptable complex, and/or a complex with a polymer).

As used herein, the terms poorly soluble drug, drug having poor solubility, and the like refer to a drug (in its neutral (i.e., uncharged) state) having a water solubility at neutral pH of less than 10 mg/ml. In some embodiments, the drug (in its neutral state) has a water solubility at neutral pH of less than 5 mg/ml. In other embodiments, the drug (in its neutral state) has a water solubility at neutral pH of less than 1 mg/ml. For example, buprenorphine base (i.e., uncharged buprenorphine) has a solubility at neutral pH of <1 mg/ml (whereas the corresponding hydrochloride salt has a solubility at neutral pH of 17 mg/ml). Thus, as used herein, buprenorphine (including buprenorphine base and its salts, hydrates, solvates, complexes, etc.) is a poorly soluble drug. Similarly, morphine base (i.e., uncharged morphine) has a solubility at neutral pH of <1 mg/ml (whereas the corresponding sulfate has a solubility at neutral pH of 64 mg/ml). Thus, as used herein, morphine (including morphine base and its salts, hydrates, solvates, complexes, etc.) is a poorly soluble drug. In a third example, oxycodone base (i.e., uncharged oxycodone) has a solubility at neutral pH of <1 mg/ml (whereas the corresponding hydrochloride has a solubility at neutral pH of 100 mg/ml). Thus, as used herein, oxycodone (including oxycodone base and its salts, hydrates, solvates, complexes, etc.) is a poorly soluble drug.

In certain embodiments, the poorly soluble drug is chosen from opioids (including opiates). Opioids include naturally-occurring, synthetic, and semi-synthetic opioids, such as, e.g., alfentanil, allylprodine, alphaprodine, anileridine, benzylmorphine, bezitramide, buprenorphine, butorphanol, clonidine, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazine, fentanyl, heroin, hydrocodone, hydromorphone, hydroxypethidine, isomethadone, ketobemidone, levallorphan, levomethadyl, levorphanol, levophenacylmorphan, lofentanil, meperidine, meptazinol, metazocine, methadone, metopon, morphine, myrophine, nalbuphine, naloxone, naltrexone, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, remifentanil, sulfentanil, tramadol, and tilidine. For example, in some embodiments, the opioid may be chosen from, e.g., buprenorphine, codeine, fentanyl, hydrocodone, hydromorphone, morphine, methylnaltrexone, nalbuphine, nalmefene, oxymorphone, oxycodone, pethidine, and tramadol.

In some embodiments, the PDS may further comprise an additional compound, such as an additional drug. The additional drug may be chosen from, e.g., opioid receptor antagonists (including µ-receptor antagonists), opioid receptor agonists (including µ-receptor agonists), mixed µ-agonists/µ-antagonists, anti-inflammatory drugs, and analgesics. In some embodiments, the second drug is an opioid receptor antagonist, such as, e.g., the µ-opioid receptor antagonist naloxone, including naloxone.HCl (naloxone hydrochloride). In some embodiments where the poorly soluble drug is an opioid analgesic, the opioid receptor antagonist is added to deter abuse of the opioid analgesic.

The poorly soluble drug may be present in an amount ranging from about <1% to about 90% of the PDS by mass. For example, the poorly soluble drug may be present in an amount ranging from about 0.01% to about 90%, about 0.01% to about 10%, about 0.2 to about 5%, about <1% to about 10%, about 0.01% to about 10%, about 0.1% to about 10%, about 0.01% to about 5%, about 0.1% to about 5%, about 0.1% to about 3%, about <1% to about 50%, about <1% to about 30%, about <1% to about 80%, about 5% to about 90%, about 10% to about 95%, or about 0.1 to about 5% of the PDS, by mass. In some embodiments, the poorly soluble drug content may be about 0.5% by mass.

In some embodiments, the stabilizer is a polymer, such as, e.g., a water-soluble polymer, a polymer of neutral charge, or a water-soluble polymer of neutral charge. In some embodiments, the stabilizer is biodegradable. In some embodiments, the stabilizer is bioerodable. In some embodiments, the stabilizer may be considered by the FDA to be generally regarded as safe (GRAS).

In some embodiments, the stabilizer is a polymer chosen from polyethylene oxide (also known as polyethylene glycol or PEG), polypropylene oxide, or copolymers thereof. In some embodiments, the stabilizer is a water-soluble polymer of neutral charge chosen from polyethylene glycol, polyvinyl alcohol, polyvinylpyrrolidone (PVP), block copolymers of ethylene oxide and propylene oxide such as, e.g., poloxamers, and tetrafunctional block copolymers derived from sequential addition of propylene oxide and ethylene oxide to ethylenediamine.

In some embodiments, the stabilizer may have an average molecular weight of about, e.g., 500, 1000, 2000, 3000, 3350, 3500, 4000, 4500, 5000, 6000, 8000, 10,000, or 100,000 Da, or an average molecular weight ranging from, e.g., about 100 Da to about 100,000 Da, about 100 Da to about 6,000 Da, about 500 Da to about 5000 Da, about 1000 Da to about 4000 Da, about 2000 Da to about 4000 Da, about 2000 Da to about 6000 Da, about 1000 Da to about 10,000 Da, or about 3000 Da to about 4000 Da.

For example, the stabilizer may be a PEG, such as a PEG of average molecular weight of about, e.g., 500, 1000, 2000, 3000, 3350, 3500, 4000, 4500, 5000, 6000, 8000, 10,000 or 100,000 Daltons. In exemplary embodiments, the stabilizer is PEG having an average molecular weight of 3350 Daltons (i.e., PEG 3350). In other embodiments, the stabilizer may be a PEG having an average molecular weight ranging from, e.g., about 100 Da to about 100,000 Da, about 100 Da to about 6,000 Da, about 500 Da to about 5000 Da, about 1000 Da to about 4000 Da, about 2000 Da to about 4000 Da, about 2000 Da to about 6000 Da, about 1000 Da to about 10,000 Da, or about 3000 Da to about 4000 Da.

In some embodiments, the composition further comprises at least one excipient, such as, e.g., a surfactant, surface stabilizer, or other enhancer. For example, in some embodiments, the composition further comprises at least one surfactant, which may be a nonionic surfactant such as, e.g., a polysorbate surfactant. In exemplary embodiments, the composition further comprises polysorbate 20 (Tween 20).

In other embodiments, the composition further comprises an emulsifier, such as, e.g., a phospholipid, propylene glycol, polysorbate, poloxamer, glyceryl monostearate, or other pharmaceutical emulsifier.

In certain embodiments, the composition comprises an opioid, a PEG, and a surfactant. In some embodiments, the invention provides a composition comprising particles of buprenorphine (such as, e.g., buprenorphine.HCl) encapsulated by PEG (which, in some embodiments, may have an average molecular weight ranging from about 500 Daltons to about 10,000 Daltons), wherein the buprenorphine content ranges from about 0.2% to about 4%. In further embodiments, the particles have an average diameter of less than 2 mm. In some embodiments, the composition further comprises a surfactant. In certain embodiments, the PDS comprises buprenorphine, PEG 3350, and Tween 20.

II. Methods of Making PDS

In some embodiments, the invention provides a first method of making a composition (such as those described in Section I) comprising particles of a poorly soluble drug encapsulated by a stabilizer, the method comprising:

blending a poorly soluble drug together with a stabilizer to form a mixture;

processing (e.g., by mixing or granulating) said mixture to form coarse particles having an average diameter ranging from about 0.1 mm to about 5 mm; and processing (e.g., by milling, grinding, or crushing) said coarse particles to form fine particles having an average diameter ranging from about 0.1 mm to about 3 mm.

In certain embodiments, the fine particles have an average diameter ranging from about 0.1 mm (100 µm) to about 3 mm. For example, the particles may have a diameter of less than 2.06 mm (corresponding to a 10 mesh sieve), less than 1.68 mm (corresponding to a 12 mesh sieve), less than 1.40 mm (corresponding to a 14 mesh sieve), less than 1.20 mm (corresponding to a 16 mesh sieve), less than 1.00 mm (corresponding to an 18 mesh sieve), less than 0.853 mm (corresponding to a 20 mesh sieve), less than 0.710 mm (corresponding to a 25 mesh sieve), less than 0.599 mm (corresponding to a 30 mesh sieve), or less than 0.500 mm (corresponding to a 35 mesh sieve). In other embodiments, the particles may have a diameter of less than 300 µm, and may be able to pass through a 50 mesh sieve. In certain embodiments, the particles have a diameter of 0.6 mm or less.

In certain embodiments, the stabilizer is heated prior to blending with the poorly soluble drug.

In other embodiments, the invention provides a second method of making a composition (such as those described in Section I) comprising particles of a poorly soluble drug encapsulated by a stabilizer. The second method uses a relatively continuous manufacturing process, which may be advantageous in certain circumstances. The second method comprises:

blending a poorly soluble drug together with a stabilizer to form a mixture;

heating said mixture to a temperature sufficient for extrusion of the mixture;

extruding said mixture to form coarse particles having an average diameter ranging from about 0.1 mm to about 5 mm;

cooling said coarse particles; and processing (e.g., by milling, grinding, or crushing) said coarse particles to form fine particles having an average diameter ranging from about 0.1 mm to about 3 mm.

In certain embodiments, the fine particles have an average diameter ranging from about 0.1 mm (100 µm) to about 3 mm. For example, the particles may have a diameter of less than 2.06 mm (corresponding to a 10 mesh sieve), less than 1.68 mm (corresponding to a 12 mesh sieve), less than 1.40 mm (corresponding to a 14 mesh sieve), less than 1.20 mm (corresponding to a 16 mesh sieve), less than 1.00 mm (corresponding to an 18 mesh sieve), less than 0.853 mm (corresponding to a 20 mesh sieve), less than 0.710 mm (corresponding to a 25 mesh sieve), less than 0.599 mm (corresponding to a 30 mesh sieve), or less than 0.500 mm (corresponding to a 35 mesh sieve). In other embodiments, the particles may have a diameter of less than 300 µm, and may be able to pass through a 50 mesh sieve. In certain embodiments, the particles have a diameter of 0.6 mm or less.

In certain embodiments, the stabilizer is heated prior to blending with the poorly soluble drug.

III. Pharmaceutical Compositions (Final Dosage Forms)

In some embodiments, the invention provides pharmaceutical compositions (sometimes referred to as final dosage forms or FDF) comprising the compositions described in Section I above.

The poorly soluble drug may be present in the pharmaceutical composition in an amount ranging from about <1% to about 90% by mass. For example, the poorly soluble drug may be present in an amount ranging from about 0.01% to about 90%, about 0.01% to about 10%, about 0.2 to about 5%, about <1% to about 10%, about 0.01% to about 10%, about 0.1% to about 10%, about 0.01% to about 5%, about 0.1% to about 5%, about 0.1% to about 3%, about <1% to about 50%, about <1% to about 30%, about <1% to about 80%, about 5% to about 90%, about 10% to about 95%, or about 0.1 to about 5% of the pharmaceutical composition by mass. In some embodiments, the poorly soluble drug content may be about 0.5% by mass.

In some embodiments, the pharmaceutical compositions further comprise a second compound, such as a second drug. The second drug may be chosen from, e.g., opioid receptor antagonists (including µ-receptor antagonists), opioid receptor agonists (including µ-receptor agonists), mixed µ-agonists/µ-antagonists, anti-inflammatory drugs, and analgesics. In some embodiments, the second drug is an opioid receptor antagonist, such as, e.g., the µ-opioid receptor antagonist naloxone, including naloxone.HCl (naloxone hydrochloride). In some embodiments where the poorly soluble drug is an opioid analgesic, the opioid receptor antagonist is added to deter abuse of the opioid analgesic. The resulting compositions may have reduced potential for abuse of the opioid, relative to compositions that do not comprise an opioid receptor antagonist.

In some embodiments, the pharmaceutical compositions further comprise at least one excipient (such as, e.g., a water-soluble polymer, surfactant, and/or enhancer), such as a pharmaceutically acceptable excipient. Examples of pharmaceutically acceptable excipients are described in *Remington's Pharmaceutical Sciences* by E. W. Martin, and include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In some embodiments, the pharmaceutical compositions also contain pH buffering reagents, and wetting or emulsifying agents.

The pharmaceutical compositions may, in some embodiments, be formulated for oral administration, for example as tablets, capsules, or other oral dosage forms. Such oral dosage forms may be prepared by conventional means. The pharmaceutical composition can also be prepared as a liquid, for example as a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration, the composition may take the form of tablets or lozenges according to conventional protocols.

For administration by oral inhalation, the compounds for use according to the present invention are conveniently delivered in the form of an aerosol spray from a pressurized pack or nebulizer (e.g., in PBS), with a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for parenteral administration (including, e.g., intravenous or intramuscular administration) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, such as, e.g., pyrogen free water.

The pharmaceutical composition can also be formulated for rectal administration as a suppository or retention enema, e.g., containing conventional suppository bases such as PEG, cocoa butter or other glycerides.

In some embodiments, the pharmaceutical compositions described herein provide improved dissolution of the poorly soluble drug, relative to the unencapsulated poorly soluble drug, and/or to another dosage form (such as, e.g., a more invasive dosage form). For example, dissolution may be increased by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by a Vankel tablet dissolution apparatus approved by the United States Pharmacopeia.

In some embodiments, the pharmaceutical compositions described herein provide improved oral bioavailability of the poorly soluble drug, relative to the unencapsulated poorly soluble drug, and/or to another dosage form (such as, e.g., a more invasive dosage form). For example, absorption may be increased by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by, e.g., in vivo pharmacokinetic studies in a preclinical animal model or human clinical evaluation.

In some embodiments, the pharmaceutical compositions described herein are immediate-release formulations. In such embodiments, the pharmaceutical compositions provide a more rapid onset of action of the poorly soluble drug, relative to the unencapsulated poorly soluble drug, and/or to another dosage form (such as, e.g., a more invasive dosage form). For example, the onset of action may be shortened by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by, e.g., in vivo pharmacokinetic studies in a preclinical animal model or human clinical evaluation.

In other embodiments, the pharmaceutical compositions described herein are controlled-release formulations. In such embodiments, the pharmaceutical compositions described herein provide a more rapid onset of action of the poorly soluble drug.

In some embodiments, the pharmaceutical compositions described herein have reduced absorption variability, relative to the unencapsulated poorly soluble drug, and/or to another dosage form (such as, e.g., a more invasive dosage form).

In some embodiments, the pharmaceutical compositions described herein are associated with improved patient compliance, relative to another pharmaceutical composition comprising the same poorly soluble drug (which may be in another dosage form, such as, e.g., a more invasive dosage form).

IV. Methods of Making Pharmaceutical Compositions

In further embodiments, the invention provides a method of making a pharmaceutical composition, comprising the first, second, or third method described in Section II above, and further comprising:

formulating the fine particles.

In certain embodiments, the fine particles are formulated into unit doses.

In embodiments in which the pharmaceutical compositions comprise at least one excipient, the invention also provides a method of making a pharmaceutical composition, comprising the first, second, or third method described in Section II above, and further comprising:

mixing the fine particles with at least one excipient to form a second mixture; and formulating the second mixture.

In certain embodiments, the fine particles are formulated into unit doses.

V. Methods of Treatment

The pharmaceutical compositions described herein are useful to treat any disease or condition for which administration of a corresponding hydrophobic drug is desirable. For example, compositions comprising opioids are useful for the treatment of pain. The terms "treat," treatment," and "treating" refer to (1) a reduction in severity or duration of a disease or condition, (2) the amelioration of one or more symptoms associated with a disease or condition without necessarily curing the disease or condition, or (3) the prevention of a disease or condition. Suitable subjects include, e.g., humans and other mammals, such as, e.g., mice, rats, dogs, and non-human primates.

In certain embodiments, the invention provides a method of treating pain, comprising administering a pharmaceutical composition described in Section III to a subject in need thereof. For example, in such embodiments, the poorly soluble drug may be chosen from, e.g., opioids, including, e.g., buprenorphine, codeine, fentanyl, hydrocodone, hydromorphone, morphine, methylnaltrexone, nalbuphine, nalmefene, oxymorphone, oxycodone, pethidine, and tramadol. Moreover, in such embodiments, the pharmaceutical composition may further comprise an opioid receptor antagonist, such as, e.g., naloxone or naltrexone, to deter abuse of the opioid analgesic.

In other embodiments, the invention provides a method of treating opiate addiction, comprising administering a pharmaceutical composition described in Section III to a subject in need thereof. For example, in such embodiments, the poorly soluble drug may be chosen from, e.g., methadone, naloxone, and naltrexone.

The following examples are intended to be purely exemplary of the present invention.

EXAMPLES

Example 1

Preparation of Buprenorphine.HCl PDS

A solution of 1 kg of autoclaved polyethylene glycol (Dow, PEG 3350, NF, FCC) and polysorbate (Tween 20, FCC), at a 10:1 mass ratio, cooled to less then 60° C., is aseptically mixed with 20 g of buprenorphine.HCl (Johnson Matthey, milled USP grade) powder. The suspension (which contains 2% buprenorphine) is then blended in a paddle mixer and further agitated using low-frequency sonication (as described in U.S. Pat. Appl. Pub. No. 2005/0175707) to form buprenorphine.HCl particles encapsulated in a PEG/Tween matrix. The powder is then frozen at −20° C. for at least 2 hours and then ground into a fine powder using a Retsch knife mill. Particles smaller than 600 μm are separated by sieving (30 mesh). Buprenorphine content is confirmed using an HPLC method.

Example 2

Preparation of Immediate-Release Oral Buprenorphine.HCl Capsules

An immediate-release oral dosage form (gelatin capsules) containing the buprenorphine.HCl particles prepared in Example 1, as well as naloxone.HCl as an abuse-deterrent second drug, is prepared as described below. The PDS prepared in Example 1 is dry mixed with naloxone (as naloxone.HCl dihydrate, USP) and additional PEG 3350 for bulking to achieve the correct capsule fill weight (400-500 mg) to achieve the desired dose. Clear gelatin #1 capsules are then filled with the mixture in a Fast-CAP Filling machine to yield capsules containing 2.0±0.2 mg buprenorphine (with respect to the free base) and 0.5±0.05 mg naloxone (with respect to the free base). The capsules thus contain buprenorphine and naloxone at a ratio of 4:1, with respect to the free bases.

Example 3

Dissolution of Immediate-Release Oral Buprenorphine.HCl Capsules

The in vivo dissolution rate of the fast-release formulation prepared in Example 2 was measured by USP Paddle Method 2 at 50 or 100 rpm in 900 ml of 0.1 N HCl acidic buffer (pH between 1.6 and 3) at 37° C. It was found that greater then 75% (by weight) of the therapeutically active agent was released after 45 minutes.

Example 4

Single-Dose Pharmacokinetic Study in Rats

The composition prepared in Example 2 (prior to loading into gelatin capsules) was administered via oral gavage once daily for 14 consecutive days to male and female F-344 rats at a low (0.03 mg/kg) or high (0.5 mg/kg) dose (n=10 each). Plasma samples collected up to 8 hours from single-dose pharmacokinetic (PK) studies in male rats (non-GLP) were compared to 14-day samples using a validated extraction and LC-MS-MS analytical method.

Values for the single-dose PK study were 0.53 and 4.07 ng/ml for male rats administered 0.03 and 0.5 mg/kg, respectively (n=3-5), observed at the first 15 minute collection time. The concentration-time profiles declined from $C_{max}$ in mono- or multi-exponential relationships. AUC values for the single-dose PK study were 2.51 and 10.33 ng/ml for male rats administered 0.03 and 0.5 mg/kg, respectively (n=3-5). At day 14 of the repeat dose toxicity study for rats administered 0.03 and 0.5 mg/kg, respectively (n=4 each), $C_{max}$ values were 1.57 and 4.11 ng/ml for males and 1.85 and 4.12 ng/ml for females, also observed at the 30 minute collection time. $C_{max}$ values were similar for males and females based on 30 minute and 8 hour time points from 14-day plasma samples analyzed. Norbuprenorphine, the main metabolite of buprenorphine, and naloxone plasma concentrations were below the limit of quantitation.

Example 5

Preparation of Pharmaceutical Compositions Comprising Oxycodone

Pharmaceutical compositions comprising oxycodone may be prepared according to the methods of the invention. The compositions may have the following characteristics:

| | |
|---|---|
| Oxycodone content | 0.1-200 mg |
| PEG 1500 content | 100-1000 mg |

Example 6

Preparation of Controlled-Release Pharmaceutical Compositions Comprising Oxycodone Controlled-release pharmaceutical compositions comprising oxycodone may be prepared according to the methods of the invention. The compositions may have the following characteristics:

| | |
|---|---|
| Oxycodone content | 0.1-200 mg |
| PVP K-30 content | 100-1000 mg |

Example 7

Preparation of Pharmaceutical Compositions Comprising Morphine

Pharmaceutical compositions comprising morphine may be prepared according to the methods of the invention. The compositions may have the following characteristics:

| | |
|---|---|
| Morphine content | 0.1-100 mg |
| Poloxamer 407 content | 100-1000 mg |

Example 8

Preparation of Controlled-Release Pharmaceutical Compositions Comprising Morphine Controlled-release pharmaceutical compositions comprising morphine may be prepared according to the methods of the invention. The compositions may have the following characteristics:

| | |
|---|---|
| Morphine content | 0.1-100 mg |
| PEG 8000 content | 100-1000 mg |

Example 9

Preparation of Pharmaceutical Compositions Comprising Hydrocodone

Pharmaceutical compositions comprising hydrocodone may be prepared according to the methods of the invention. The compositions may have the following characteristics:

| | |
|---|---|
| Hydrocodone content | 0.1-100 mg |
| PEG 3350 content | 100-1000 mg |

Example 10

Preparation of Pharmaceutical Compositions Comprising Dihydrocodone

Pharmaceutical compositions comprising dihydrocodone may be prepared according to the methods of the invention. The compositions may have the following characteristics:

| | |
|---|---|
| Dihydrocodone content | 0.1-100 mg |
| PEG 3350 content | 100-1000 mg |

Example 11

Preparation of Pharmaceutical Compositions Comprising Codeine

Pharmaceutical compositions comprising codeine may be prepared according to the methods of the invention. The compositions may have the following characteristics:

| | |
|---|---|
| Codeine content | 0.1-100 mg |
| Poloxamer 407 content | 100-1000 mg |

Example 12

Preparation of Pharmaceutical Compositions Comprising Meperidine

Pharmaceutical compositions comprising meperidine may be prepared according to the methods of the invention. The compositions may have the following characteristics:

| | |
|---|---|
| Meperidine content | 0.1-500 mg |
| PEG 3350 content | 100-1000 mg |

Example 13

Preparation of Pharmaceutical Compositions Comprising Propoxyphene

Pharmaceutical compositions comprising propoxyphene may be prepared according to the methods of the invention. The compositions may have the following characteristics:

| | |
|---|---|
| Propoxyphene content | 0.1-500 mg |
| PEG 3350 content | 100-1000 mg |

Example 14

Preparation of Pharmaceutical Compositions Comprising Levorphanol

Pharmaceutical compositions comprising levorphanol may be prepared according to the methods of the invention. The compositions may have the following characteristics:

| | |
|---|---|
| Levorphanol content | 0.1-100 mg |
| Poloxamer 407 content | 100-1000 mg |

Example 15

Preparation of Pharmaceutical Compositions Comprising Oxymorphone

Pharmaceutical compositions comprising oxymorphone may be prepared according to the methods of the invention. The compositions may have the following characteristics:

| | |
|---|---|
| Oxymorphone content | 0.1-200 mg |
| PEG 3350 content | 100-1000 mg |

Example 16

Preparation of Pharmaceutical Compositions Comprising Hydromorphone

Pharmaceutical compositions comprising hydromorphone may be prepared according to the methods of the invention. The compositions may have the following characteristics:

| | |
|---|---|
| Hydromorphone content | 0.1-100 mg |
| Poloxamer 407 content | 100-1000 mg |

Example 17

Preparation of Pharmaceutical Compositions Comprising Fentanyl

Pharmaceutical compositions comprising hydromorphone may be prepared according to the methods of the invention. The compositions may have the following characteristics:

| Fentanyl content | 0.1-500 mg |
|---|---|
| PEG 3350 content | 100-1000 mg |

Example 18

Preparation of Pharmaceutical Compositions Comprising Alfentanyl

Pharmaceutical compositions comprising alfentanyl may be prepared according to the methods of the invention. The compositions may have the following characteristics:

| Alfentanyl content | 0.01-50 µg |
|---|---|
| PEG 3350 content | 100-1000 mg |

Example 19

Preparation of Pharmaceutical Compositions Comprising Sufentanyl

Pharmaceutical compositions comprising sufentanyl may be prepared according to the methods of the invention. The compositions may have the following characteristics:

| Sulfentanyl content | 0.01-500 µg |
|---|---|
| PEG 3350 content | 100-1000 mg |

Example 20

Preparation of Pharmaceutical Compositions Comprising Remifentanyl

Pharmaceutical compositions comprising remifentanyl may be prepared according to the methods of the invention. The compositions may have the following characteristics:

| Remifentanyl content | 0.01-500 µg |
|---|---|
| PEG 3350 content | 100-1000 mg |

Example 21

Preparation of Pharmaceutical Compositions Comprising Levomethadyl

Pharmaceutical compositions comprising levomethadyl may be prepared according to the methods of the invention. The compositions may have the following characteristics:

| Levomethadyl content | 0.01-200 mg |
|---|---|
| Poloxamer 407 content | 100-1000 mg |

Example 22

Preparation of Pharmaceutical Compositions Comprising Methadone

Pharmaceutical compositions comprising methadone may be prepared according to the methods of the invention. The compositions may have the following characteristics:

| Methadone content | 0.01-200 mg |
|---|---|
| PEG 3350 content | 100-1000 mg |

Example 23

Preparation of Pharmaceutical Compositions Comprising Butorphanol

Pharmaceutical compositions comprising butorphanol may be prepared according to the methods of the invention. The compositions may have the following characteristics:

| Butorphanol content | 0.1-200 mg |
|---|---|
| PEG 3350 content | 100-1000 mg |

Example 24

Preparation of Pharmaceutical Compositions Comprising Dezocine

Pharmaceutical compositions comprising dezocine may be prepared according to the methods of the invention. The compositions may have the following characteristics:

| Dezocine content | 0.1-200 mg |
|---|---|
| Poloxamer 407 content | 100-1000 mg |

Example 25

Preparation of Pharmaceutical Compositions Comprising Nalbuphine

Pharmaceutical compositions comprising nalbuphine may be prepared according to the methods of the invention. The compositions may have the following characteristics:

| Nalbuphine content | 0.1-200 mg |
|---|---|
| PEG 3350 content | 100-1000 mg |

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

The invention claimed is:

1. A particle delivery system (PDS) comprising dry particles having an average diameter of less than about 2 mm, wherein the dry particles comprise a poorly soluble drug and a stabilizer comprising polyethylene glycol (PEG), wherein
the amount of the poorly soluble drug present in the dry particles ranges from about 0.2% to about 4% by mass of the dry particles,
the poorly soluble drug is encapsulated by the stabilizer,
the poorly soluble drug comprises at least one drug selected from codeine, fentanyl, hydrocodone, hydromorphone, morphine, methylnaltrexone, nalbuphine, nalmefene, oxymorphone, oxycodone, pethidine, tramadol, and combinations or mixtures thereof,
and wherein the stabilizer is water soluble.

2. The composition of claim 1, wherein the PEG has an average molecular weight ranging from about 100 Daltons to about 100,000 Daltons.

3. The PDS of claim 2, wherein the PEG is PEG 3350.

4. The PDS of claim 1, further comprising a surfactant.

5. The PDS of claim 4, wherein the surfactant is a nonionic surfactant.

6. A pharmaceutical composition comprising the PDS of claim 1 and at least one second compound.

7. The pharmaceutical composition of claim 6, wherein the composition is formulated for oral administration.

8. The pharmaceutical composition of claim 6, wherein the at least one second compound is a drug chosen from opioid receptor antagonists, anti-inflammatory drugs, analgesics, and combinations or mixtures thereof.

9. The pharmaceutical composition of claim 8, wherein the drug comprises an opioid receptor antagonist.

10. The pharmaceutical composition of claim 9, wherein the drug comprises naloxone or a pharmaceutically acceptable salt thereof.

11. The pharmaceutical composition of claim 10, wherein the naloxone salt is naloxone HCl.

* * * * *